United States Patent [19]

Harding et al.

[11] Patent Number: 4,618,855
[45] Date of Patent: Oct. 21, 1986

[54] SOIL POLLUTION MONITORING SYSTEM

[75] Inventors: Robert C. Harding, Dallas; Edward H. Olsen, Farmersville, both of Tex.

[73] Assignee: Genelco, Inc., Dallas, Tex.

[21] Appl. No.: 681,575

[22] Filed: Dec. 14, 1984

[51] Int. Cl.⁴ .............................................. G08B 21/00
[52] U.S. Cl. ....................................... 340/605; 73/40; 73/49.2; 340/518; 340/632
[58] Field of Search .............. 340/605, 632, 633, 518, 340/523; 73/40, 40.5, 49.2

[56] References Cited
U.S. PATENT DOCUMENTS
3,209,343 9/1965 Dunham et al. ................. 340/518 X Primary Examiner—James L. Rowland
Assistant Examiner—Daniel Myer
Attorney, Agent, or Firm—Cushman, Darby & Cushman

[57] ABSTRACT

A soil pollution monitoring system includes a plurality of ducts for conveying gases and air past a sensing device. The sensing device detects selected compounds in the gases and air and provides an output in electrical form which indicates whether or not the levels of certain compounds in the gases and air are greater than a threshold amount thereby indicating that a leak has occurred.

6 Claims, 5 Drawing Figures

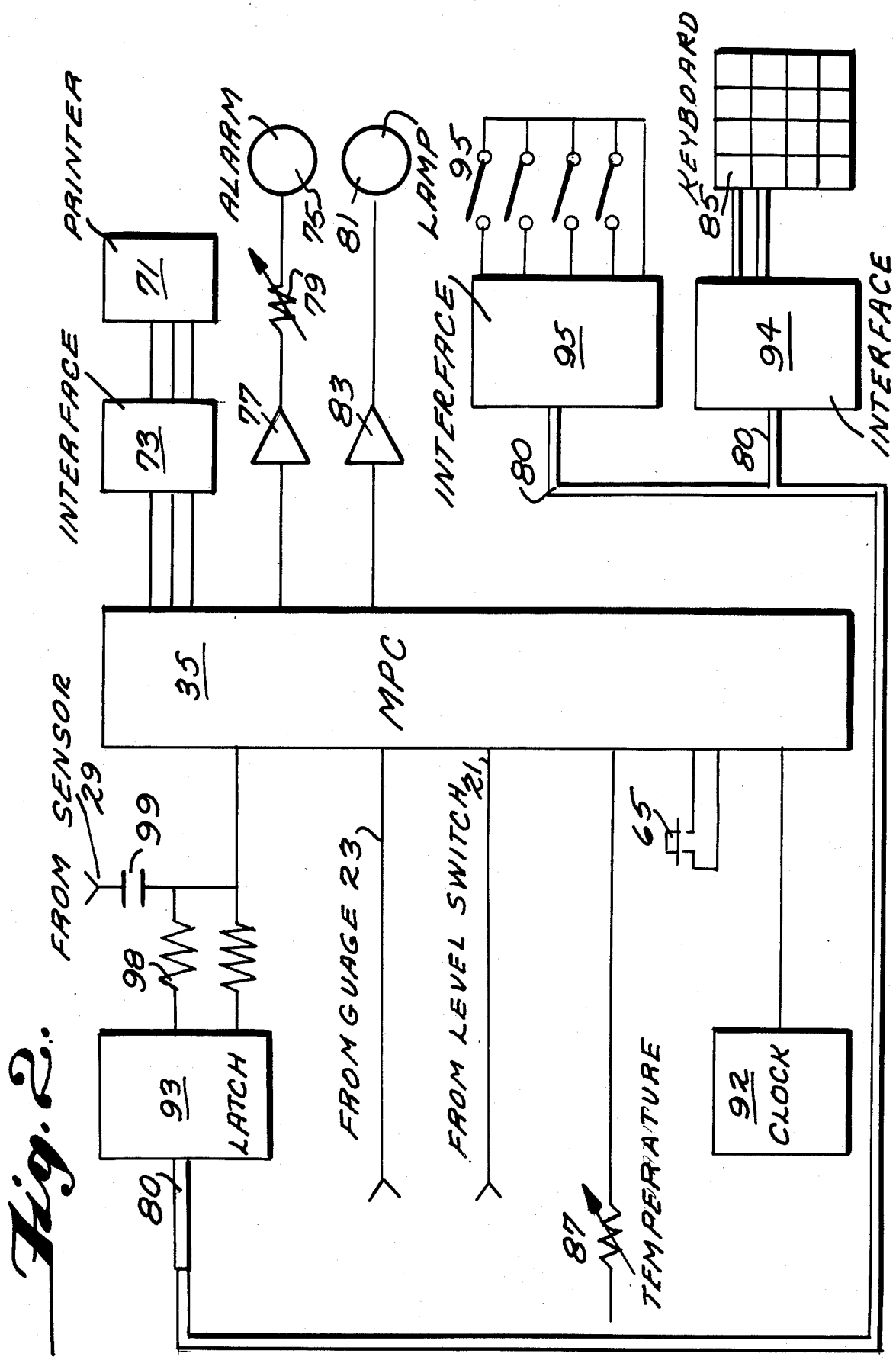

SOIL POLLUTION MONITORING SYSTEM

BACKGROUND OF THE INVENTION

The present invention relates to an underground soil pollution monitoring system for monitoring the integrity of underground fuel storage tanks.

Numerous attempts have been made to monitor underground pollution caused by leaks in tanks, pipelines or other containers of hazardous chemicals. A number of detection systems have been proposed such as in Murray U.S. Pat. No. 3,995,472 wherein a pair of insulated conductors adjacent a buried pipeline detect leakage by degradation of the insulation for the electrical conductors. A short circuit of the conductors will occur when the insulation is degraded. Thus, in this system two insulated conductors are required throughout the length of the sensor which, of course, is expensive. Moreover, should a break exist in one of the sensors, between a leak and the monitor, the system would be ineffective to detect a leakage. More recently, Klein disclosed in U.S. Pat. No. 4,305,068 an enclosure about a tank or pipe wherein the enclosure is filled with a liquid and two electrodes are placed in the enclosure in contact with the liquid. When leakage occurs in the presence of the container, the container degrades and the level of fluid inside the tube falls thereby breaking a circuit between the electrodes.

Other leakage detection systems have been developed which use an electrical grid network for locating leaks, such as described in Johnson U.S. Pat. No. 4,404,516.

None of these prior art devices have been capable of detecting low level, long term leakage of fuel in an underground environment in a safe reliable manner. Accordingly, it is an object of invention to provide an improved soil pollution monitoring system.

SHORT STATEMENT OF THE INVENTION

Accordingly, this invention relates to a plurality of ports positioned in various locations proximate tanks and fuel lines. A vacuum pump draws air and leakage gases through each port, in sequence. The air and leakage gas is passed through a sensor which detects the presence of gasoline, carbon monoxide, methane, propane, ethanol, freon and hydrogen, among others. Depending upon the level of the gases detected a signal is provided to a computer which generates an alarm signal indicating that the gasses detected exceed a preset level.

After each port is connected to the sensor under the vacuum, the system is cleaned by forcing fresh air through the sensor. A background port is provided from which the combinatorial effect of ambient gases can be established. This establishes a reference level for determining if the detected leakage gasses exceed such a level that a leakage is confirmed.

BRIEF DESCRIPTION OF THE DRAWINGS

Other objects, features and advantages of the present inventions will become more fully apparent from the following detailed description of the preferred embodiment, the appended claims and the accompanying drawings in which:

FIG. 2 is a schematic illustration of electronic control circuit of the preferred embodiment of the present invention.

DETAILED DESCRIPTION OF THE PREFERRED EMBODIMENT

Figure 1:
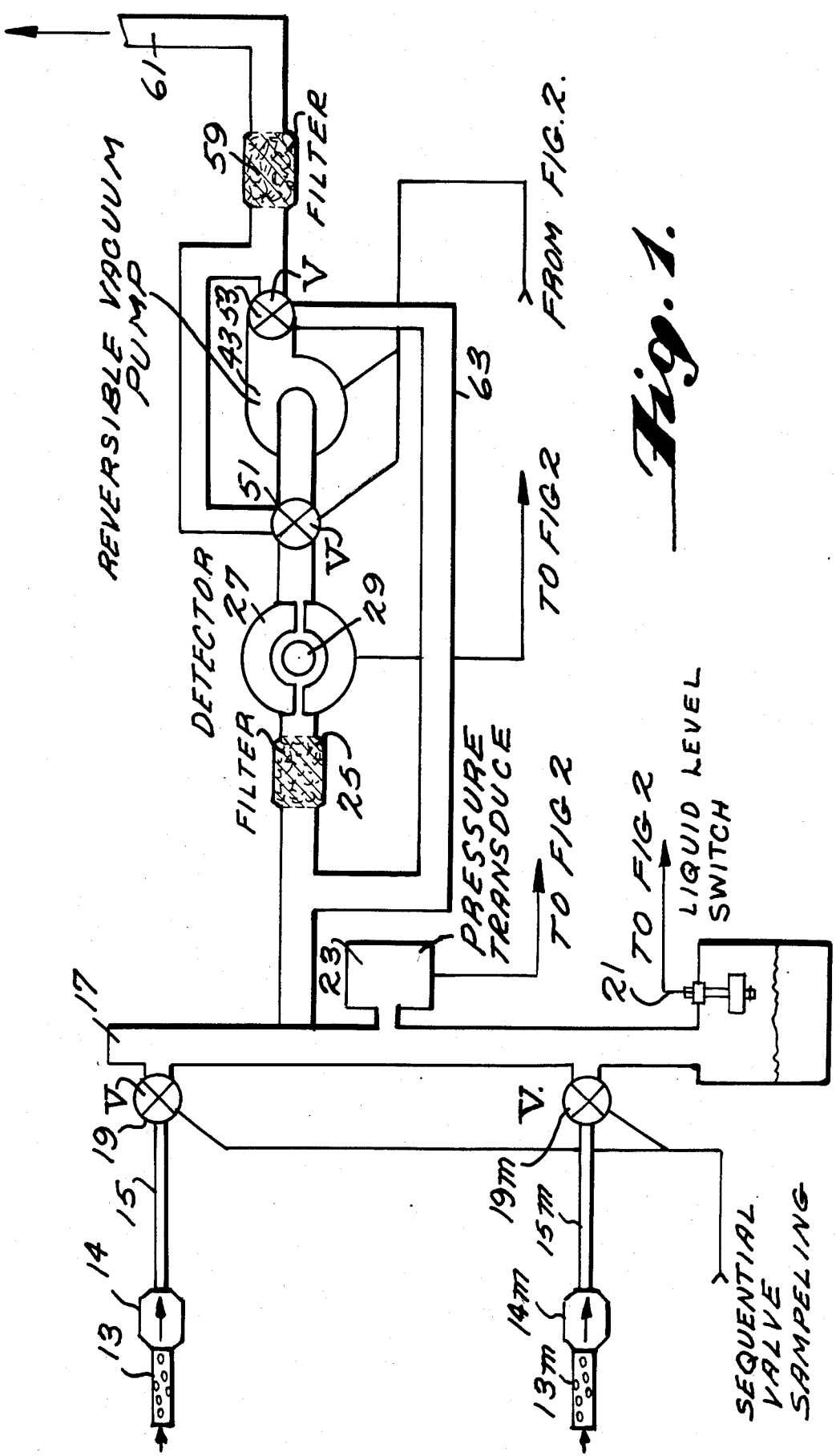
FIG. 1 is a schematic illustration of the preferred embodiment of the monitoring system of the present invention.

Refer now to the FIG. 1 which illustrates a series of sampling tubes 13–13m which are generally positioned underground in the neighborhood of tanks, pipes, and other containments from which leakage of liquids or vapors are to be detected. A portion of the leakage vapors, or a portion of the vaporized components of the leakage liquids, are drawn into these sampling tubes by means described below; the relative concentration of such vapors in the air surrounding a given sampling tube being related to the quantity of leakage, the rate of leakage, the distance between the sampling tube and the leakage, the nature of the leakage material, and other lesser effects. The number of sampling tubes will depend on the number and size of tanks, pipes, and containments to be monitored. The configuration of said sampling tubes may be such as a slotted small diameter pipe that might be placed in the soil near the containment or tank being monitored, or it might be a simple tube with a fitting to attach to a multiwalled tank, whereby the interstitial space between the walls could be monitored.

Connected to each sampling tube 13 is a flow conditioner 14. The flow conditioner filters particulate matter from the air/vapor sample and presents a fixed pneumatic restriction to the sample as it is drawn through the flow conditioner. A one way valve within the flow conditioner reduces the restriction to air which may be blown out of the sampling tube 13. The system, as will later be shown, measures the vacuum restrictions and will compensate for such abnormalities as liquid rather than air/vapor samples being present, cut or pinched transport tube 15, etc.

Transport tubes 15–15m conduct the air/vapor samples from flow conditioners 14–14m to valves 19–19m and alternately conduct air in the reverse direction.

An additional set including sampling tube 13, flow conditioner 14, transport tube 15, and valve 19 is installed to sample an area which presents a representative level of ambient vapors, but not localized leakage vapors. The sample vapors obtained via this one path are used to calibrate the machine and compensate for changes in the environment, such as smog, ozone, etc., which could otherwise degrade system accuracy.

Another path, in which sampling tube 13, flow conditioner 14, and transport tube 15 are of a different physical configuration serves as means to induce known vapor mixtures into the machine for the purpose of verification of calibration and other maintenance tests.

The valves 19–19m connect, generally in a sequential manner, the transport tubes 15–15m to a single collection manifold 17, the design of which separates the air/vapor samples from any liquid which may have been entrapped due to condensation, or for any of reason, in the transport tubes 15–15m.

Liquid level switch 21 operates if the liquid trapped in the manifold 17 exceeds a predetermined level. The pressure transducer 23 provides a signal which indicates the pressure or vacuum level of the manifold 17. Numerous information on system performance is contained therein. Measuring the vacuum level with all valves 19–19m closed can provide early warning of leaking valves or a failing vacuum source. Remeasuring the vacuum level with a particular valve 19 open an all other valves 19–19m closed verifies that the particular sample path of transport tube 15 and flow conditioner 14 are not blocked and not leaking, and that sample tube 13 is not immersed in liquid.

Filters 25 and 59 remove particulate matter that may have entered various system components during installation or may be introduced through the exhaust port 61. It will be shown that the exhaust port 61 normally vents the sampled vapors from the system, but also is used as the inlet for air when the system blows down the sample paths 13–13m, 14–14m, and 15–15n.

Air/vapor samples from the manifold 17 pass through the filter 25 and into the cavity 27 which is rendered explosion proof by the choice of thick, strong walls, sturdy fasteners, and long small diameter channels for the inlet of, and withdrawal of, the air/vapor sample. Mounted within this cavity is the vapor sensing element 29. In the preferred embodiment a Panasonic type EYHS-130P02 gas sensor comprised of sintered semi-conductive materials, primarily oxides of iron is the vapor sensing element 29. This sensor presents an electrical resistance which varies as the result of its adsorption of various gasses. The varying resistance of the vapor sensing element 29 is monitored by an analog to digital input port of the microcomputer 35 as referenced in FIG. 2.

The vacuum pump 43 provides the pressure reduction necessary to transport the air/vapor samples through the system described. The pressure/flow characteristics of the vacuum pump 43 are chosen to cause significant changes in the vacuum levels in the manifold 17 as a result of deviations from the normal pneumatic restriction within the sampling path 13, 14, and 15.

A set of valves 51 and 53 are included to reverse the flow of air or air/vapor mixture within the system. This allows the same vacuum pump 43 to function as a blowdown pump which effectively performs such functions as forcing condensate in transport tubes 15–15m down and out of the system through the flow conditioners 14–14m and sampling tubes 13–13m, and forcing any dangerously high concentration of vapors back down the same path away from the system and operators.

Turn now to FIG. 2 which is an illustration of the circuitry utilized in the preferred embodiment of the present invention for controlling the soil pollution monitoring system of the present invention. The operation of the aforementioned system is controlled by a microcomputer system 35. The level of liquid in the manifold 19 is monitored and when it reaches a predetermined level, a signal is provided indicating that the manifold needs to be drained. In addition the pressure level in the manifold 17 is monitored and checked for abnormal values.

The microcomputer in the preferred embodiment is a Motorola MC68705R3. This unit receives signals from the monitoring system of FIG. 1 and provides certain output data on a periodic basis. Thus, at the output of the microcomputer is a conventional output device, the printer 71 which is driven by an interface circuit 73. Alarm signaling is done by a sound transducer 75 which is driven by an amplifier 77 through the volume adjustment potentiometer 79. Additional alarm signaling is done by a lamp 81 which is driven by amplifier 83. As will be explained more fully below, a keyboard 85 is provided for operator intervention in system operation.

The keyboard is used to set the real time clock 92 and calendar of the system as well as calling for various test modes and service functions, such as feeding printer paper. Specific combinations of key operations will allow monitoring of specific port conditions on a real time basis, will allow calibration checks to be performed, will allow the alarm lamp to be cleared, and will cause the initiation of various manufacturing test and burn-in routines. The keyboard 85 is connected to the microcomputer data buss 80 through interface element 94 which may selectively connect or disconnect the keyboard from the data buss. Several status switches 91 are included to allow such initial configuration choices as the maximum number of ports to be operated, the alarm threshold level for vapor, the choice of causing the unit to pause when transport tubes might freeze, and the choice of optimizing certain ports for specific contaminants. The simplest form of said optimization being the increase of sensitivity for ports which will be sensing the area around a diesel tank; diesel having a lower vaporization rate than gasoline. The status switches 91 are coupled to the data buss 80 through interface element 95 which operates in the above described manner of interface element 94. The external reset button 65, allows disabling of the alarm tone without any effect on the alarm lamp.

Temperature sensor 87 presents a varying resistance to the microcomputer 35 analog input. This sensor is used to determine whether the transport tubes 15–15m might be subject to excessive condensation or freezing of vapors being carried therein. Resistors 98–98n are driven by latch circuit 93 which is driven by the microcomputer data buss. The resistors 98–98n may be driven to ground, to a positive voltage, or may be driven by an extremely high impedance by the latch 93. The net result is that a pulsating signal between ground and some positive reference voltage may be applied to capacitor 99 through a selected resistance value, because the resistors 98–98n which are connected to high impedance terminals of latch 93 are effectively disconnected. In the preferred embodiment eight resistors which are related as are the adjacent positions in the binary numbering system, are used to yield a resistance range of about 250:1. The resistance of this pulse can be matched to the specific sensor and the specific background vapor conditions such that a predetermined voltage pulse appears at the input of the microcomputer 35, when the calibration routine is exercised, due to the resistance divider action between resistors 98–98n and the vapor sensor. The capacitor is sufficiently large that it appears as a very low impedance during the pulse, but causes the average dc current through the vapor sensor 29 to be zero.

Figure 3A:
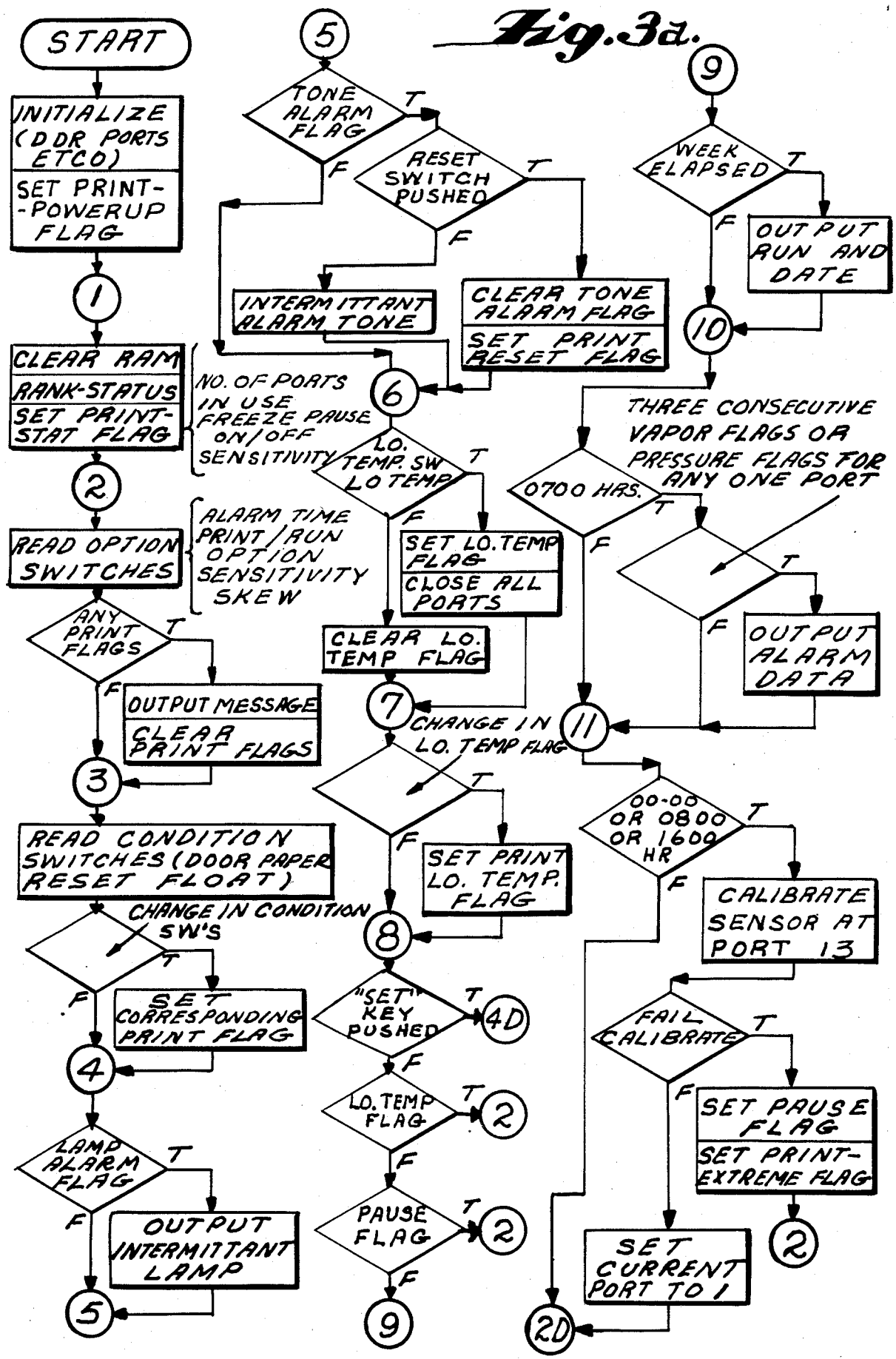
FIG. 3 is a flow diagram illustration of the operation sequence of the preferred embodiment of the present invention.
Figure 3B:
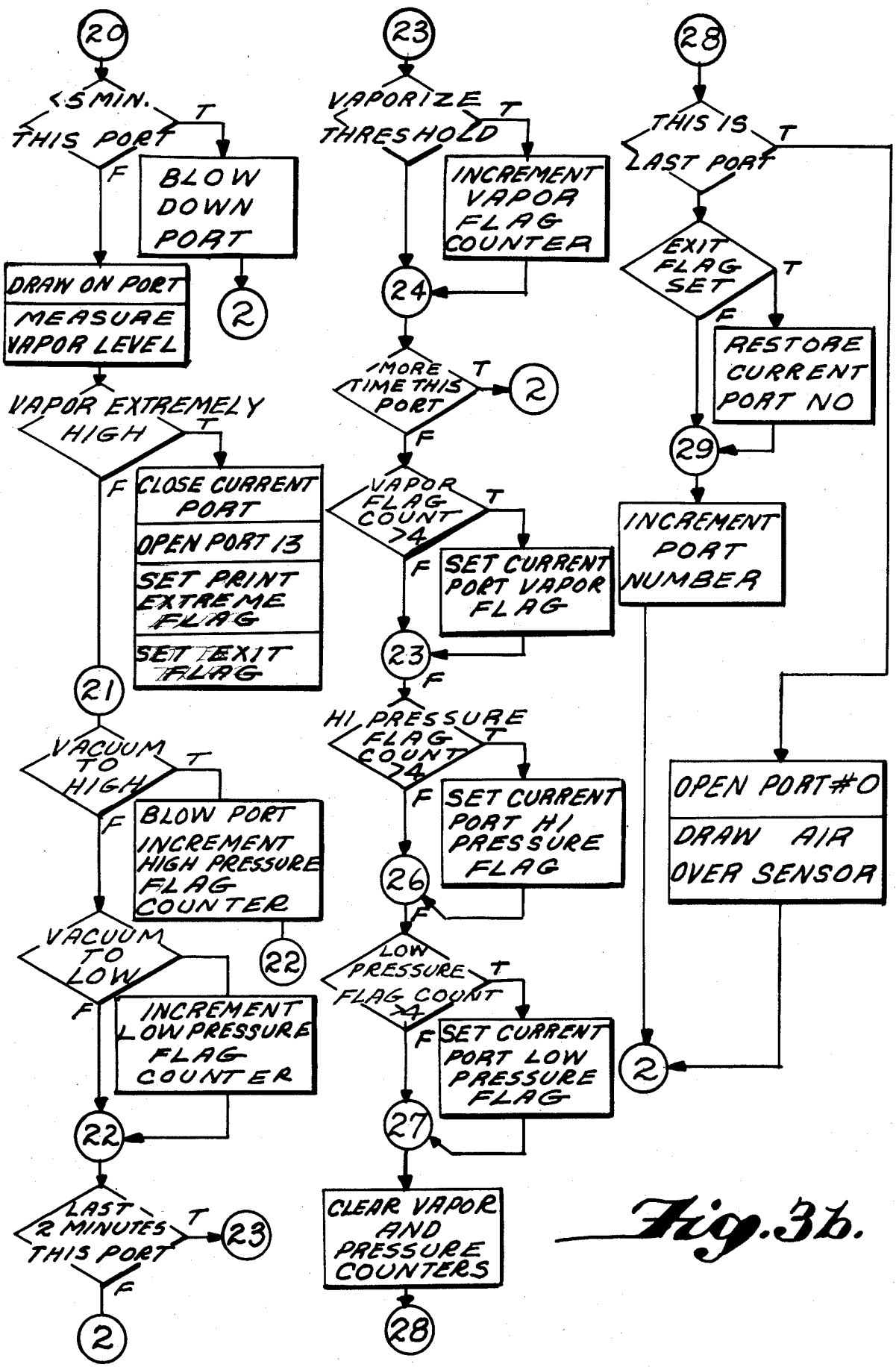
Figure 3C:
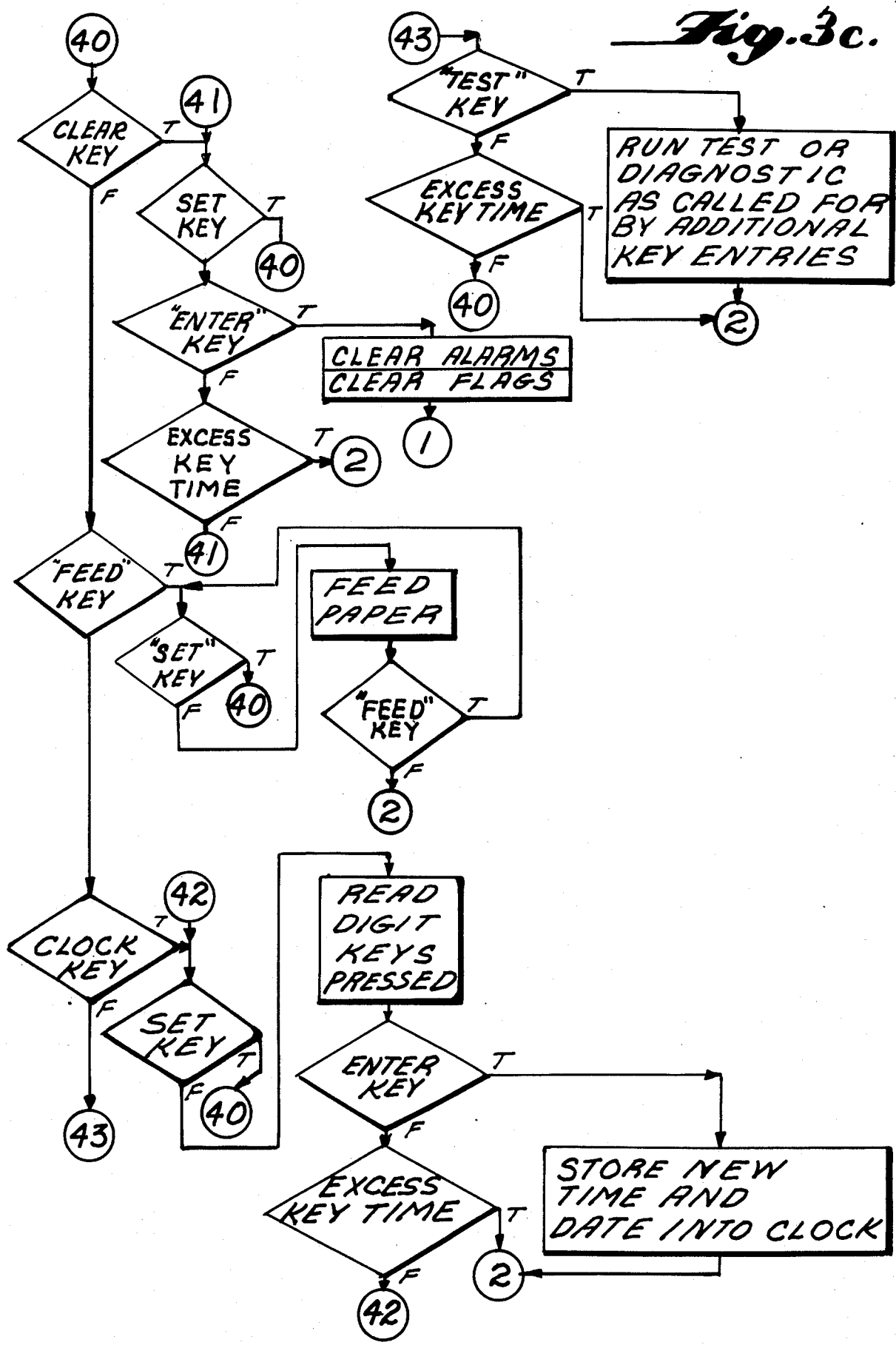

Now refer to the flow drawing of operation sequences and decisions, FIG. 3. The first action after power-up is initialization of the system, partially between start and node 1 and more fully between nodes 1 and 2. Node two is the top of the normal operating loop. Between nodes 2 and 3 options switches are verified and any real time printing is done. After node three the system condition switches are read and any corresponding printout requirement flags are set. Next the audible and lit alarm indicators are operated if necessary and the audible alarm reset if the external reset button is pressed. After node 7 the ambient temperature is checked and a low temperature pause decision is made on the basis of temperature and whether the low temperature pause option is selected. After node 8 the keyboard is checked for activation of the 'set' key. If the key is pressed the system exits to the keyboard routine which will be described later. If the key was not pressed system checks for two flags either of which will terminate the loop and send the system back to node 2. If the loop is not terminated the system then determines whether the weekly operating statement needs to be printed, then whether it is time to print the daily alarm summary. After node 11 the system determines whether it is one of the three daily self calibrate periods, and attempts the calibration if due. At node 20 the system blows down the selected port for 5 minutes to clear condensate and reduce carry over from any previous high vapor concentration in the sensor. The system then draws the sample from the selected port while constantly watching for any sign of extremely high or dangerous vapor levels. If vapor levels approaching lower explosive limit are encountered the active port is closed and fresh air is drawn into the system to purge the high vapor concentration. After node 21 the vacuum level limits are checked and appropriate action taken. After node 23 the normal measurement of vapor concentration is made and any that indicate a leak are counted during the last two minutes of the port period. On the last pass for the current port the pressure and vapor faults that happened 5 or more times in the last two minutes are counted as single flags. The blocks below node 28 merely update the active port for the various conditions that can exist at that time.

The keyboard routine is shown on sheet 3 of FIG. 3. The clear key causes alarms and flags to be cleared. The feed key causes paper advancement. The clock key causes the clock to be set if the proper numeric data are entered. The test key allows access to various diagnostic routines. Note that the excess key time blocks prevent the machine from inadvertently being left in a state in which it is not monitoring.

The microcomputer is programmed by normal computing techniques to operate in accordance with the aforementioned plan. Accordingly a listing of the code has not been included herein.

The present invention has been disclosed in connection with a preferred embodiment thereof. It should be appreciated, however, that other embodiments of the invention may be developed which fall within the spirit and scope of the invention as defined by the following claims.

What is claimed is:

1. A soil pollution monitoring system comprising:
a plurality of ducts for conveying air and gases;
a sensor means for detecting selected compounds in said air and gases;
means for drawing said gases and air past said sensor means;
means for sequentially connecting said sensor means to each of said ducts and applying said drawing means to draw said air and gases through said connected duct past said sensor means;
means for establishing an ambient level of said selected compounds in said gases and air;
means for comparing said detected, selected compounds with said ambient level of said selected compounds; and
means for generating an alarm signal when the level of the detected, selected compounds exceeds said ambient level by a predetermined level.

2. The soil pollution monitoring system of claim 1 further comprising means for detecting the vacuum level in said ducts, and means for determining if the vacuum level in said ducts is above or below a predetermined vacuum range.

3. The soil pollution monitoring system of claim 1 further comprising means for purging said sensor means of said gases after said gases have been determined to be present in sufficient concentration to require purging.

4. The soil pollution monitoring system of claim 3 further comprising means for detecting when said ducts leak, are restricted, or are beginning to transport liquid material.

5. The soil pollution monitoring system of claim 1 further comprising distributed ends for said ducts; and such distributed ends being located proximate the containments being monitored.

6. The soil pollution monitoring system of claim 1 further comprising the location of an end of said ducts in an interstitial cavity of multiwall containments.

* * * * *